(12) United States Patent
Nakatani et al.

(10) Patent No.: US 10,989,647 B2
(45) Date of Patent: Apr. 27, 2021

(54) ORALLY DISINTEGRATING TABLET EVALUATING METHOD, AND ORALLY DISINTEGRATING TABLET EVALUATING DEVICE

(71) Applicant: SAWAI PHARMACEUTICAL CO., LTD., Osaka (JP)

(72) Inventors: Masatoshi Nakatani, Osaka (JP); Masaru Sugita, Osaka (JP); Nobuaki Ikeji, Osaka (JP); Kenji Nozawa, Osaka (JP)

(73) Assignee: SAWAI PHARMACEUTICAL CO., LTD., Osaka (JP)

(*) Notice: Subject to any disclaimer, the term of this patent is extended or adjusted under 35 U.S.C. 154(b) by 304 days.

(21) Appl. No.: 16/170,789

(22) Filed: Oct. 25, 2018

(65) Prior Publication Data

US 2019/0064047 A1 Feb. 28, 2019

Related U.S. Application Data

(63) Continuation of application No. PCT/JP2017/016529, filed on Apr. 26, 2017.

(30) Foreign Application Priority Data

Apr. 26, 2016 (JP) .............................. JP2016-088219

(51) Int. Cl.
*G01N 5/02* (2006.01)
*G01N 15/08* (2006.01)
(Continued)

(52) U.S. Cl.
CPC ......... *G01N 15/0826* (2013.01); *G01N 1/286* (2013.01); *G01N 5/02* (2013.01);
(Continued)

(58) Field of Classification Search
None
See application file for complete search history.

(56) References Cited

U.S. PATENT DOCUMENTS 2,575,169 A * 11/1951 Green, Jr. .............. G01N 5/045
73/73
3,952,584 A * 4/1976 Lichstein ............... G01N 13/00
73/73
(Continued)

FOREIGN PATENT DOCUMENTS

| JP | 2008-64620 A | 3/2008 |
| JP | 2010-164415 A | 7/2010 |
| JP | 2013-35824 A | 2/2013 |

OTHER PUBLICATIONS

Yunxia Bi et al., "Preparation and Evaluation of Directly Compressed Tablets Rapidly Disintegrating in the Oral Cavity", Pharm Tech Japan, Nov. 1998, p. 111(1723)-p. 170(1782), vol. 14, No. 11, Japan, prior art cited in the present application.
(Continued)

*Primary Examiner* — Alexander A Mercado
(74) *Attorney, Agent, or Firm* — Hauptman Ham, LLP

(57) ABSTRACT

Provided is an orally disintegrating tablet evaluating method includes: measuring the mass of tablet; placing the tablet on a preparation placement surface of a test solution supply unit; measuring a water absorption time for a test solution to penetrate from one end of the tablet in contact with the surface to the other end of the tablet; measuring the mass of the tablet for which the time for the solution to penetrate has been measured; and calculating the water absorption rate of the tablet by the following formula (1); wherein the tablet is evaluated based on a water absorption rate of the tablet of 0.004 g/sec:

water absorption rate of tablet=(mass of tablet after measurement of time for solution to penetrate–
(Continued)

mass of tablet before measurement of time for solution to penetrate)/(time for solution to penetrate from one end to other end) (1).

8 Claims, 8 Drawing Sheets

(51) Int. Cl.
*G01N 33/15* (2006.01)
*G01N 1/28* (2006.01)
*A61K 9/20* (2006.01)
*A61K 9/00* (2006.01)
*G01N 33/00* (2006.01)

(52) U.S. Cl.
CPC ............ *G01N 5/025* (2013.01); *G01N 33/15* (2013.01); *A61K 9/0056* (2013.01); *A61K 9/20* (2013.01); *A61K 9/2018* (2013.01); *G01N 2033/0077* (2013.01)

(56) References Cited

U.S. PATENT DOCUMENTS

| | | | | |
|---|---|---|---|---|
| 4,357,827 A | * | 11/1982 | McConnell | G01N 5/02 137/408 |
| 2009/0241640 A1 | * | 10/2009 | Kallmes | G01N 5/025 73/38 |
| 2011/0063433 A1 | * | 3/2011 | Thonhauser | G01N 21/251 348/135 |

OTHER PUBLICATIONS

International Search Report (PCT/ISA/210) dated Jul. 4, 2017 for the PCT application No. PCT/JP2017/016529, with English translation.

Written Opinion of the International Search Authority dated Jul. 4, 2017 for the PCT application No. PCT/JP2017/016529.

Bi, Yunxia et al., "Preparation and Evaluation of a Compressed Tablet Rapidly Disintegrating in the Oral Cavity", Chemical and Pharmaceutical Bulletin, 1996, vol. 44, No. 11, p. 2121-2127, Pharmaceutical Society of Japan.

Asami Kashima et al., "Evaluation of Quality of Orodispersible Famotidine Tablets", Iryo Yakugaku, 2006, vol. 32, No. 6, pp. 511 to 516.

Kenji Ogata et al., "Evaluation on Disintegration Tests of Rapidly-Disintegrating Tablets", Iryo Yakugaku, 2001, vol. 27, No. 6, pp. 553 to 558.

English translation of Written Opinion of the International Search Authority dated Jul. 4, 2017 for the PCT application No. PCT/JP2017/016529.

Office Action issued for corresponding Japanese Patent Application No. 2018-514662 dated Jan. 26, 2021, along with an English machine translation.

Atsushi Kaminishi et al., "Studies on new orally disintegrating tablets manufacturing by agitation granulation [V].—Loperamide hydrochloride used as a model drug-", Research on Home Medicines, 2016, vol. 35, pp. 39-48, along with an English machine translation.

* cited by examiner

ORALLY DISINTEGRATING TABLET EVALUATING METHOD, AND ORALLY DISINTEGRATING TABLET EVALUATING DEVICE

CROSS REFERENCE TO RELATED APPLICATIONS

This application is based upon and claims the benefit of priority from the prior Japanese Patent Application No. 2016-088219, filed on Apr. 26, 2016, and PCT Application No. PCT/JP2017/016529, filed on Apr. 26, 2017, the entire contents of which are incorporated herein by reference.

FIELD

The present invention relates to an orally disintegrating tablet evaluating method and an orally disintegrating tablet evaluating device. In particular, the present invention relates to an evaluating method for evaluating the disintegration property of an orally disintegrating tablet and an evaluating device for an orally disintegrating tablet.

BACKGROUND

An orally disintegrating tablet is a solid preparation which is quickly disintegrated in oral cavity with saliva in the cavity or a small amount of water and easy to take. For this reason, demand for orally disintegrating tablets which patients easily take is increasing. Orally disintegrating tablets are desired to be disintegrated quickly with only saliva in oral cavity or with a small amount of water in about 30 seconds to 40 seconds or less. However, in order to study the preparation of orally disintegrating tablets, a proper evaluating method for evaluating the disintegration property of the orally disintegrating tablet is necessary.

The disintegration time of the orally disintegrating tablet can be measured by an oral disintegration tester sold from each manufacturer (TriCorp Tester manufactured by Okada Seiko Co., Ltd., or the like), but the results are different depending on the test conditions. Therefore, it is necessary to set appropriate conditions considering the disintegration test time in human oral cavity. In addition, in the method of measuring the disintegration time in human oral cavity, it is difficult to obtain reproducibility because there are variations depending on individual differences and physical conditions of humans to be tested. For this reason, it is hard to say that the method of measuring the disintegration time in human oral cavity is an appropriate evaluating method.

Furthermore, for an orally disintegrating tablet containing a highly active drug substance, it is difficult to measure in oral cavity of humans. For this reason, there is a need for an evaluating method that can substitute the method of measuring the disintegration time in human oral cavity.

From such a problem, for example, a method for evaluating the disintegration property of an orally disintegrating tablet by measuring the water absorption time of the tablet is known. It is known that by using this method, a good correlation between the oral disintegration time and the water absorption time can be obtained in the similar formulation system (Yunxia Bi, Hisakazu Sunada, PHARM TECH JAPAN, 14 (11), 1723 (1998)). For example, after obtaining a correlation between the oral disintegration time of a drug substance-free orally disintegrating tablet and the water absorption time, the oral disintegration time can be evaluated from the water absorption time of the orally disintegrating tablet containing the drug substance.

SUMMARY

The oral disintegration time and the water absorption time of the orally disintegrating tablet are correlated in the similar formulation system. Here, the similar formulation system refers to a preparation in which the types of excipients to be formulated are the same or similar, and also the manufacturing methods are the same or similar. However, correlation is not necessarily obtained for orally disintegrating tablets with different formulation systems, so it is not appropriate as a general-purpose tool for evaluating the disintegration property of orally disintegrating tablets. Generally, it is known that there are various techniques in the preparation and the production method of orally disintegrating tablets, and its disintegration mechanism is also diverse. In the development of preparations, there is a necessity to choose an appropriate technique according to the characteristics of the active ingredient, or to develop new technologies or the like, and it is difficult to develop the preparation only with the similar formulation system. Therefore, it is desirable to be able to evaluate the disintegration property of orally disintegrating tablets in any formulation system in order to compare the investigation products prototyped by various preparation designs and determine the optimal preparation.

One object of the present invention is to provide an evaluating method capable of appropriately evaluating the disintegration property in an orally disintegrating tablet of any formulation system. Another object of the present invention is to provide an evaluating device capable of appropriately evaluating the disintegration property in an orally disintegrating tablet of any formulation system.

One embodiment of the present invention provides a method of evaluating an orally disintegrating tablet comprising: measuring the mass of an orally disintegrating tablet; placing the orally disintegrating tablet on a preparation placement surface of a test solution supply unit; measuring a water absorption time for a test solution to penetrate from one end of the orally disintegrating tablet in contact with the preparation placement surface to the other end of the orally disintegrating tablet; measuring the mass of the orally disintegrating tablet for which the time for the test solution to penetrate has been measured; and calculating the water absorption rate of the orally disintegrating tablet by the following formula (1); wherein the orally disintegrating tablet is evaluated based on a water absorption rate of the orally disintegrating tablet of 0.004 g/sec:

water absorption rate of orally disintegrating tablet= (mass of orally disintegrating tablet after measurement of time for test solution to penetrate– mass of orally disintegrating tablet before measurement of time for test solution to penetrate)/(time for test solution to penetrate from one end to other end of orally disintegrating tablet)  (1).

In the orally disintegrating tablet evaluating method, the oral disintegration time of the orally disintegrating tablet may be separately measured, and the reciprocal of the oral disintegration time of the orally disintegrating tablet may be plotted with respect to the water absorption rate of the orally disintegrating tablet, to obtain a correlation curve between the water absorption rate of the orally disintegrating tablet and the reciprocal of the oral disintegration time.

In the orally disintegrating tablet evaluating method, the water absorption rate of the orally disintegrating tablet for obtaining the oral disintegration time may be calculated, and an oral disintegration time corresponding to the water absorption rate of the orally disintegrating tablet for obtaining the oral disintegration time may be obtained from the correlation curve.

In the orally disintegrating tablet evaluating method, the orally disintegrating tablet may have a shape having a major axis and a minor axis crossing the major axis, the orally disintegrating tablet may be placed on the preparation placement surface of the test solution supply unit so that the major axis direction of the orally disintegrating tablet is substantially parallel to the preparation placement surface of the test solution supply unit, and the water absorption time for the test solution to penetrate from one end of the orally disintegrating tablet in contact with the preparation placement surface to the other end of the orally disintegrating tablet furthest away from the one end in the minor axis direction of the orally disintegrating tablet may be measured.

In the orally disintegrating tablet evaluating method, penetration of the test solution to the other end of the orally disintegrating tablet may be judged by a change in the color tone of the other end of the orally disintegrating tablet.

Also, according to one embodiment of the present invention, an orally disintegrating tablet, wherein the water absorption rate of the orally disintegrating tablet evaluated by any orally disintegrating tablet evaluating method described above is 0.004 g/sec or more, is provided.

Also, according to one embodiment of the present invention, there is provided an orally disintegrating tablet evaluating device including a test solution supply unit, a water absorption time measuring unit and an analysis unit, wherein the test solution supply unit supplies a test solution to one end of an orally disintegrating tablet in contact with a preparation placement surface, the water absorption time measuring unit measures a water absorption time for the test solution to penetrate from one end of the orally disintegrating tablet to the other end of the orally disintegrating tablet, and the analysis unit calculates the water absorption rate of the orally disintegrating tablet by the following formula (1) using the mass of the orally disintegrating tablet and the mass of the orally disintegrating tablet for which the time for the test solution to penetrate has been measured, and evaluates the orally disintegrating tablet based on a water absorption rate of the orally disintegrating tablet of 0.004 g/sec:

> water absorption rate of orally disintegrating tablet=
> (mass of orally disintegrating tablet after measurement of time for test solution to penetrate−
> mass of orally disintegrating tablet before measurement of time for test solution to penetrate)/(time for test solution to penetrate from one end to other end of orally disintegrating tablet) (1).

In the orally disintegrating tablet evaluating device, the analysis unit may receive an input of the oral disintegration time of the orally disintegrating tablet, and may provide a correlation curve between the water absorption rate of the orally disintegrating tablet and the reciprocal of the oral disintegration time.

In the orally disintegrating tablet evaluating device, the analysis unit may calculate the water absorption rate of the orally disintegrating tablet to obtain the oral disintegration time, and may calculate the oral disintegration time corresponding to the water absorption rate of the orally disintegrating tablet to obtain the oral disintegration time from the correlation curve.

In the orally disintegrating tablet evaluating device, the water absorption time measuring unit may measure the color tone of the other end of the orally disintegrating tablet, and the analysis unit may judge that the test solution has penetrated to the other end of the orally disintegrating tablet based on a change in the color tone of the other end of the orally disintegrating tablet.

REFERENCE SIGNS LIST

1 . . . sample,
100 . . . evaluating device,
110 . . . test solution supply unit,
111 . . . sample storage unit,
113 . . . test solution supply member,
120 . . . water absorption time measuring unit,
130 . . . analysis unit,
140 . . . control unit,
150 . . . mass measuring unit,
160 . . . input unit,
170 . . . display unit.

DESCRIPTION OF EMBODIMENTS

Hereinafter, the orally disintegrating tablet evaluating method and the orally disintegrating tablet evaluating device according to the present invention will be described. However, the orally disintegrating tablet evaluating method and the orally disintegrating tablet evaluating device of the present invention are not to be construed as being limited to the descriptions of the embodiments and examples described below.

(Orally Disintegrating Tablet Evaluating Device)

Figure 1A:
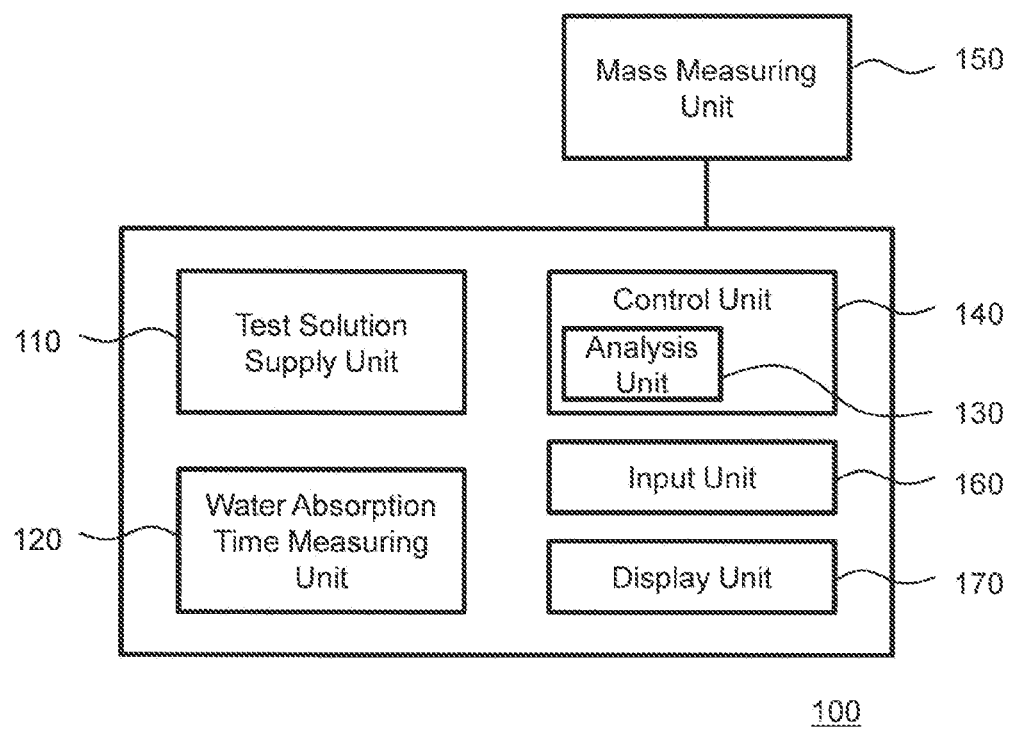
FIG. 1A is a schematic view showing an orally disintegrating tablet evaluating device 100 according to one embodiment of the present invention.
Figure 1B:
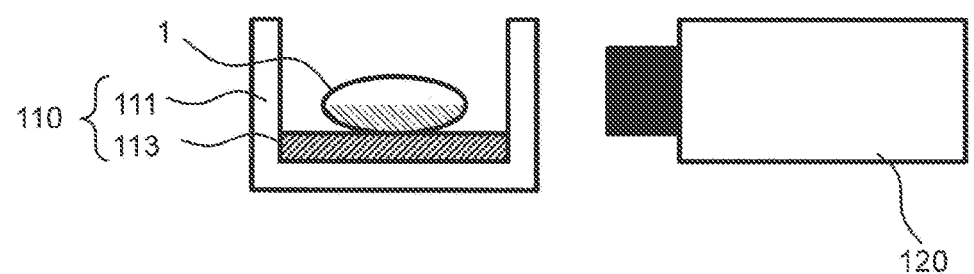
FIG. 1B is a schematic view showing an orally disintegrating tablet evaluating device 100 according to one embodiment of the present invention.

FIGS. 1A and 1B are schematic views showing an orally disintegrating tablet evaluating device 100 according to one embodiment of the present invention. FIG. 1A is a block diagram of the orally disintegrating tablet evaluating device 100 and FIG. 1B is a schematic view showing a test solution supply unit 110 and a water absorption time measuring unit 120. The orally disintegrating tablet evaluating device 100 includes, for example, but not limited to, a test solution supply unit 110, a water absorption time measuring unit 120 and an analysis unit 130.

The test solution supply unit 110 has, for example, a sample storage unit 111 and a test solution supply member 113 arranged on the inner bottom face of the sample storage unit 111. The sample storage unit 111 is a container for storing the sample 1 on the test solution supply member 113. The sample storage unit 111 may be, for example, a petri dish or a funnel. Also, for the purpose of removing excess test solution from the test solution supply member 113, a funnel is preferable as the sample storage unit 111. For the water absorption time measuring unit 120 to measure the water absorption time of the sample 1, the sample storage unit 111 is preferably composed of a transparent member. The sample storage unit 111 is preferably composed of, for example, glass or a transparent resin. In addition, the test solution supply unit 110 may be provided with a non-open storage that accommodates the sample storage unit 111. Incidentally, it is preferable that the temperature and humidity of the space inside the sample storage unit 111 are constant. The temperature of the space inside the sample storage unit 111 may be room temperature or about 37° C. close to body temperature. For ease of operation, the temperature of the space inside the sample storage unit 111 is preferably room temperature.

The test solution supply member 113 is a member arranged on the inner bottom face of the sample storage unit 111 and providing a preparation placement surface for holding the sample 1 and is a member for supplying the test solution to one end of the sample 1. The test solution supply member 113 is a member having water retentivity for supplying the test solution to the sample 1, and examples thereof include a filter paper, a tissue paper, a paper wipe, a gel, a porous body, and the like. Also, the test solution supply member 113 contains a predetermined amount of test solution. The orally disintegrating tablet as the sample 1 generally has a shape having a major axis and a minor axis crossing the major axis, but the present invention is not limited thereto. In the case where the sample 1 has such a shape, it is preferable that the sample 1 is placed on the preparation placement surface of the test solution supply member 113 so that the major axis direction of the sample 1 is substantially parallel.

Water, artificial saliva, buffer solution and the like can be used as the test solution, but the test solution is not limited thereto. Further, in order to make it easy to discriminate a change in the color tone of the orally disintegrating tablet as the test solution penetrates, the test solution may contain a dye. In the case of evaluating general orally disintegrating tablets, about 5 ml of the test solution to be injected into the test solution supply member 113 may be permissible.

The water absorption time measuring unit 120 measures the water absorption time for the test solution to penetrate from one end of the orally disintegrating tablet arranged as the sample 1 to the other end of the orally disintegrating tablet furthest away from the one end in the short axis direction of the orally disintegrating tablet. For this, the water absorption time measuring unit 120 photographs at least the other end of the orally disintegrating tablet and transmits the image data to the analysis unit 130. The water absorption time measuring unit 120 is, for example, an image sensor for measuring the color tone of the orally disintegrating tablet. The water absorption time measuring unit 120 is, for example, a CCD image sensor or a CMOS image sensor. As shown in FIG. 1B, the water absorption time measuring unit 120 is preferably arranged outside the test solution supply unit 110. When the sample storage unit 111 is a non-open type container containing a petri dish or a funnel, a water absorption time measuring unit 120 may be disposed in a non-open type container at a position where a petri dish or a funnel can be observed.

The analysis unit 130 is a device that analyzes image data and the like received from the water absorption time measuring unit 120, and is, for example, an arithmetic device that processes an analysis program. The analysis unit 130 may be a dedicated device having a ROM (Read Only Memory) storing an analysis program or may be a general-purpose device which stores an analysis program or is provided with an analysis program online. The analysis unit 130 may be, for example, a personal computer (PC) or a portable terminal such as a tablet capable of executing an analysis program.

The analysis unit 130 analyzes a change in the color tone of the other end of the orally disintegrating tablet from the image data received from the water absorption time measuring unit 120. The analysis unit 130 can determine that the test solution has penetrated to the other end of the orally disintegrating tablet, based on a change in the color tone of the other end of the orally disintegrating tablet received from the water absorption time measuring unit 120. Depending on the amount of the penetrated test solution, a gradation of color shade may occur partially on the surface of the orally disintegrating tablet. Therefore, the analysis unit 130 may determine that the test solution penetrates to the other end of the orally disintegrating tablet with the predetermined lightness or chroma as a threshold value. The water absorption time may be visually measured without disposing the water absorption time measuring unit 120.

In addition, the analysis unit 130 calculates the water absorption rate of the orally disintegrating tablet by the following formula (1) using the mass of the orally disintegrating tablet and the mass of the orally disintegrating tablet for which the time for the test solution to penetrate has been measured.

water absorption rate of orally disintegrating tablet=
(mass of orally disintegrating tablet after measurement of time for test solution to penetrate−mass of orally disintegrating tablet before measurement of time for test solution to penetrate)/(time for test solution to penetrate from one end to other end of orally disintegrating tablet)    (1).

The analysis unit 130 may receive an input of the oral disintegration time of the orally disintegrating tablet measured separately, and may provide a correlation curve between the water absorption rate of the orally disintegrating tablet and the reciprocal of the oral disintegration time. As a result of examination, the present inventors found for the first time that the water absorption rate of the orally disintegrating tablet and the reciprocal of the oral disintegration time show a good straight line correlation. From this fact, by using the correlation curve between the water absorption rate of the orally disintegrating tablet and the reciprocal of the oral disintegration time thereof, the analysis unit 130 can calculate the reciprocal of the oral disintegration time from the water absorption rate of an orally disintegrating tablet of any formulation system whose oral disintegration time is unknown and can predict the oral disintegration time from the reciprocal.

The oral disintegration time of the orally disintegrating tablet is preferably within 40 seconds, more preferably within 30 seconds. The present inventors found for the first time that an oral disintegration time within 40 seconds can be achieved if the water absorption rate of the orally disintegrating tablet is 0.004 g/sec or more, from the correlation between the water absorption rate of the orally disintegrating tablet and the oral disintegration time thereof. In addition, it was found for the first time that if the water absorption rate of the orally disintegrating tablet is 0.006 g/sec or more, an oral disintegration time within 30 seconds can be achieved. From this, the analysis unit 130 can evaluate the orally disintegrating tablet based on a water absorption rate of the orally disintegrating tablet of 0.004 g/sec, preferably 0.006 g/sec. For example, if the orally disintegrating tablet evaluating device 100 is equipped with a display device, it is possible to prompt attention to the user by coloring the numerical value or making it bold so as to estimate suitability for an orally disintegrating tablet for which the water absorption rate has been measured, based on a water absorption rate of the orally disintegrating tablet of 0.004 g/sec.

The orally disintegrating tablet evaluating device 100 further includes a control unit 140 for controlling the water absorption time measuring unit 120. The control unit 140 may be a dedicated device having a ROM (Read Only Memory) storing a control program for controlling the water absorption time measuring unit 120 or may be a general-purpose device which stores a control program or is provided with a control program online. The control unit 140 may be, for example, a personal computer (PC) or a portable terminal such as a tablet capable of executing a control program.

Also, the control unit 140 may include the analysis unit 130, or may be installed in the orally disintegrating tablet evaluating device 100 separately from the analysis unit 130. Therefore, the analysis unit 130 may be a module embedded in the control unit 140, or may be a program executable by the control unit 140.

Further, the orally disintegrating tablet evaluating device 100 includes an input unit 160 such as, for example, a keyboard, a touch panel, a mouse, and the like. The orally disintegrating tablet evaluating device 100 receives inputs of the mass of the orally disintegrating tablet before penetration of the test solution and the mass of the orally disintegrating tablet for which the time for the test solution to penetrate has been measured, from the input unit 160. As described above, the analysis unit 130 can calculate the water absorption rate of the orally disintegrating tablet using the mass of the orally disintegrating tablet and the mass of the orally disintegrating tablet for which the time for the test solution to penetrate has been measured.

Also, the orally disintegrating tablet evaluating device 100 includes a display unit 170. The display unit 170 may be a display panel disposed on the orally disintegrating tablet evaluating device 100, or may be a display connected via a cable to the orally disintegrating tablet evaluating device 100. The orally disintegrating tablet evaluating device 100 can display the water absorption rate of the orally disintegrating tablet, a correlation curve between the water absorption rate of the orally disintegrating tablet and the reciprocal of the oral disintegration time, a correlation curve between the water absorption rate of the orally disintegrating tablet and the oral disintegration time, an image of the color tone change of the other end of the orally disintegrating tablet photographed by the water absorption time measuring unit 120, and the like, on the display unit 170, thereby allowing the user to perceive them.

The orally disintegrating tablet evaluating device 100 may be provided with a mass measuring unit 150 as shown in FIG. 1A. The mass measuring unit 150 is, for example, an electronic balance, and measures the mass of the orally disintegrating tablet. The mass of the orally disintegrating tablet measured with the mass measuring unit 150 may be input to the orally disintegrating tablet evaluating device 100 by the above-mentioned input unit 160. Also, the mass measuring unit 150 may be wired or wirelessly connected to the orally disintegrating tablet evaluating device 100 and the analysis unit 130 may capture the mass data of the orally disintegrating tablet measured by the mass measuring unit 150.

As explained above, the orally disintegrating tablet evaluating device 100 according to the embodiment of the present invention can provide a correlation curve between the water absorption rate of the orally disintegrating tablet and the reciprocal of the oral disintegration time or a correlation curve between the water absorption rate of the orally disintegrating tablet and the oral disintegration time, and can predict the oral disintegration time from the water absorption rate of the orally disintegrating tablet whose oral disintegration time is unknown. Further, it is possible to judge suitability of the preparation for the orally disintegrating tablet for which the water absorption rate has been measured, based on a water absorption rate of the orally disintegrating tablet of 0.004 g/sec.

(Orally Disintegrating Tablet Evaluating Method)

The orally disintegrating tablet evaluating method using the above-described orally disintegrating tablet evaluating device will be described below.

In order to obtain a correlation curve between the water absorption rate of the orally disintegrating tablet and the reciprocal of the oral disintegration time, arbitrary orally disintegrating tablets are prepared. Although it is possible to obtain a correlation curve if there are three or more orally disintegrating tablets, it is preferable to increase as much as possible from the viewpoint of the accuracy and reproducibility of the correlation curve. The mass of the orally disintegrating tablet to obtain the correlation curve is measured. The measured mass of the orally disintegrating tablet may be input to the orally disintegrating tablet evaluating device 100, or the orally disintegrating tablet evaluating device 100 may capture the data of the mass of the orally disintegrating tablet measured by the mass measuring unit 150.

Figure 2:
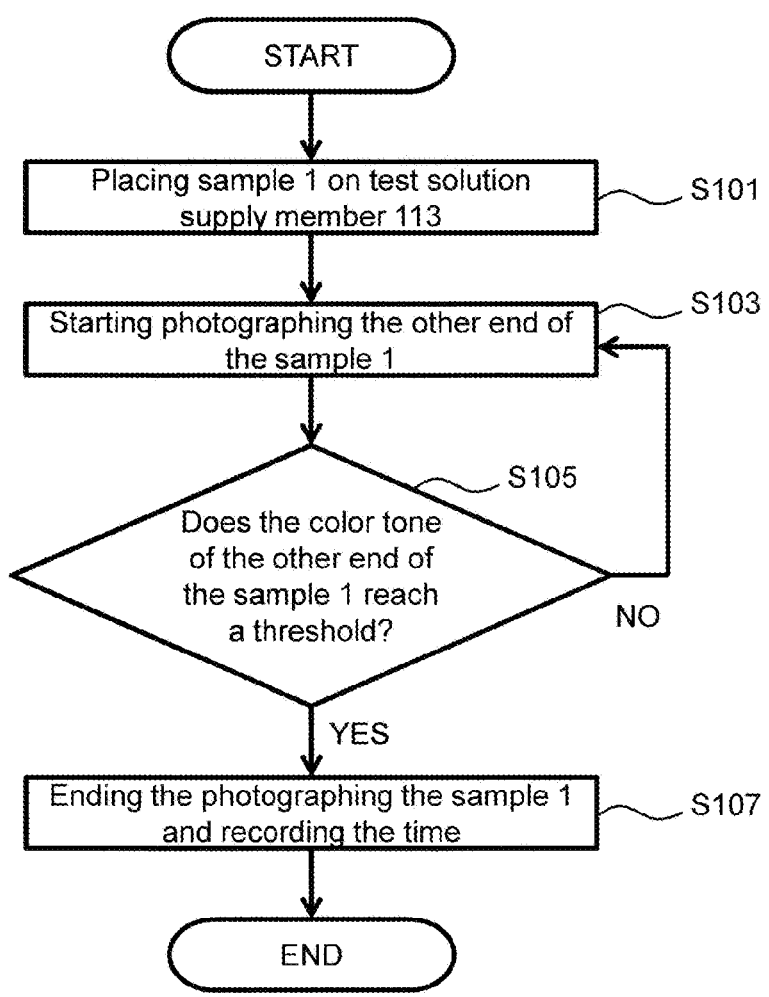
FIG. 2 is a flowchart showing a method for measuring the water absorption time according to one embodiment of the present invention.

FIG. 2 is a flowchart showing a method for measuring the water absorption time according to one embodiment of the present invention. A test solution is injected into the test solution supply member 113 arranged in the sample storage unit 111 of the test solution supply unit 110. In the case of evaluating general orally disintegrating tablets, about 5 ml of the test solution to be injected into the test solution supply member 113 may be permissible.

The sample 1 is placed on the test solution supply member 113 (S101). The water absorption time measuring unit 120 starts photographing at least the other end of the orally disintegrating tablet and transmits the image data to the analysis unit 130 (S103). The analysis unit 130 records the measurement start time.

Using the image data received from the water absorption time measuring unit 120, the analysis unit 130 analyzes a change in the color tone of the other end of the orally disintegrating tablet (S105). Depending on the amount of penetrated test solution, a gradation of color shade may occur partially on the surface of the orally disintegrating tablet. Therefore, the analysis unit 130 may determine that the test solution has penetrated to the other end of the orally disintegrating tablet with the predetermined lightness or chroma as a threshold value.

At the time when the lightness or chroma of the other end of the orally disintegrating tablet reaches a predetermined threshold value, the analysis unit 130 records the measurement end time and the water absorption time measuring unit 120 ends the photographing (S107).

Figure 3:
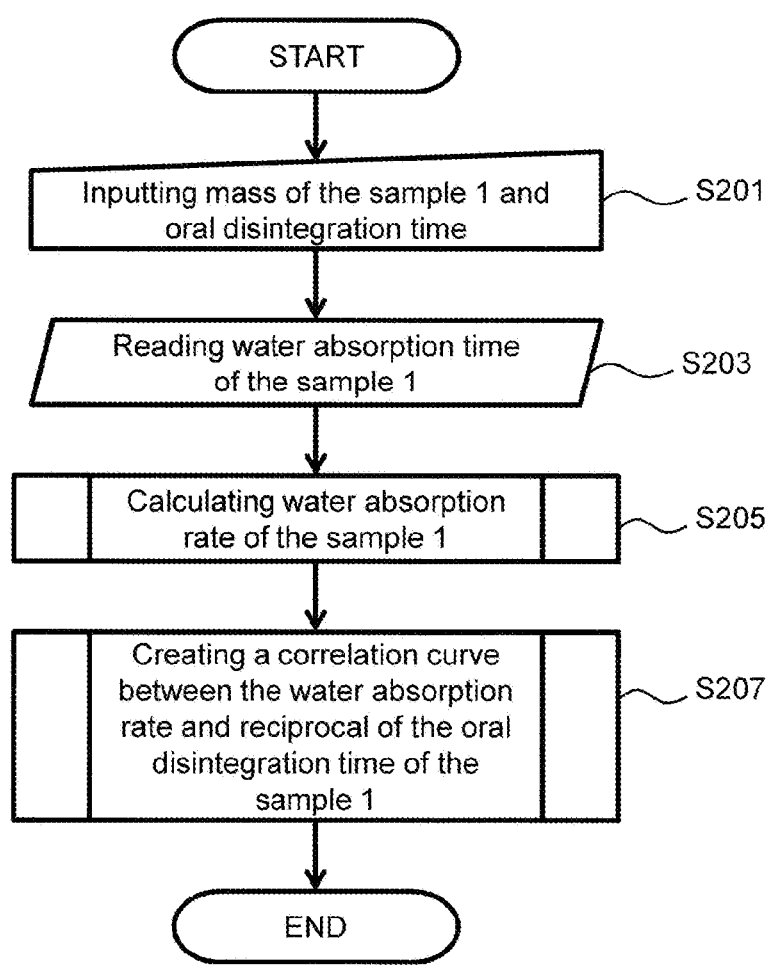
FIG. 3 is a flowchart showing a method of making a correlation curve between the water absorption rate of an orally disintegrating tablet and the oral disintegration time thereof according to one embodiment of the present invention.

FIG. 3 is a flow chart showing a method of making a correlation curve between the water absorption rate of an orally disintegrating tablet and the oral disintegration time thereof according to one embodiment of the present invention. The user of the orally disintegrating tablet evaluating device 100 measures the mass of the orally disintegrating tablet after measurement of the water absorption time and inputs the measured value to the orally disintegrating tablet evaluating device 100. In addition, the user inputs the oral disintegration time of the orally disintegrating tablet to the orally disintegrating tablet evaluating device 100 (S201). The data of the mass of the orally disintegrating tablet before measurement of the water absorption time may be input at this point, and the oral disintegration time of the orally disintegrating tablet may be previously input to the orally disintegrating tablet evaluating device 100 before measurement of the water absorption time.

The analysis unit 130 reads the measured water absorption time of the orally disintegrating tablet (S203). The analysis unit 130 calculates the water absorption rate of the orally disintegrating tablet using the following formula (1), using the mass of the orally disintegrating tablet and the mass of the orally disintegrating tablet for which the time for the test solution to penetrate has been measured (S205).

water absorption rate of orally disintegrating tablet= (mass of orally disintegrating tablet after measurement of time for test solution to penetrate−mass of orally disintegrating tablet before measurement of time for test solution to penetrate)/(time for test solution to penetrate from one end to other end of orally disintegrating tablet)    (1).

The analysis unit 130 creates a correlation curve between the water absorption rate of the orally disintegrating tablet and the oral disintegration time thereof. In addition, the analysis unit 130 creates a correlation curve between the water absorption rate of the orally disintegrating tablet and the reciprocal of the oral disintegration time thereof (S207).

Using the correlation curve between the water absorption rate of the orally disintegrating tablet and the reciprocal of the oral disintegration time thereof, the analysis unit 130 can calculate the reciprocal of the oral disintegration time from the water absorption rate of an orally disintegrating tablet of any formulation system whose oral disintegration time is unknown and can predict the oral disintegration time from the reciprocal.

Figure 4:
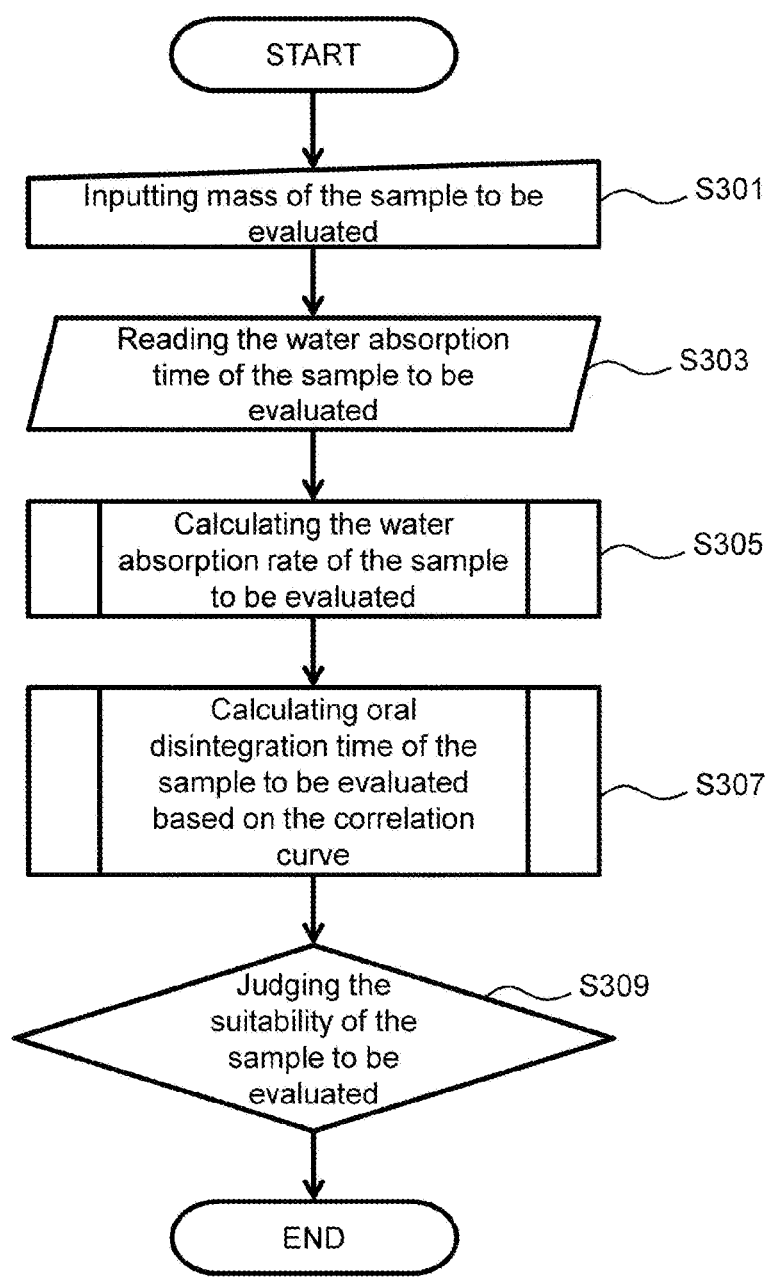
FIG. 4 is a flow chart showing a method for predicting the oral disintegration time from the water absorption rate of an orally disintegrating tablet according to one embodiment of the present invention.

FIG. 4 is a flow chart showing a method for predicting the oral disintegration time from the water absorption rate of the orally disintegrating tablet according to one embodiment of the present invention. The mass of the sample to be evaluated is measured, and the mass data is input to the orally disintegrating tablet evaluating device 100 (S301). The analysis unit 130 reads the water absorption time of the sample to be evaluated obtained by the above-described water absorption time measuring method (S303). The analysis unit 130 calculates the water absorption rate of the sample to be evaluated by the method described above (S305).

The analysis unit 130 calculates an oral disintegration time corresponding to the calculated water absorption rate of the sample to be evaluated, using a correlation curve between the water absorption rate of the orally disintegrating tablet and the reciprocal of the oral disintegration time thereof. The analysis unit 130 can provide the calculated oral disintegration time of the sample to be evaluated, as a predicted value of the oral disintegration time, to the user (S307). In addition, the analysis unit 130 can judge the suitability of the preparation for an orally disintegrating tablet whose water absorption rate has been measured, based on a water absorption rate of the orally disintegrating tablet of 0.004 g/sec, and provide it to the user (S309).

As explained above, by using the orally disintegrating tablet evaluating method according to the embodiment of the present invention, a correlation curve between the water absorption rate of the orally disintegrating tablet and the reciprocal of the oral disintegration time and a correlation curve between the water absorption rate of the orally disintegrating tablet and the oral disintegration time can be provided and the oral disintegration time can be predicted from the water absorption rate of the orally disintegrating tablet whose oral disintegration time is unknown. In addition, it is possible to judge suitability of the preparation for an orally disintegrating tablet whose water absorption rate has been measured, based on a water absorption rate of the orally disintegrating tablet of 0.004 g/sec, and to provide it to the user.

EXAMPLES

The orally disintegrating tablet evaluating method according to the present invention described above will be illustrated more in detail by specific examples and test results.

An orally disintegrating tablet was prepared and its mass was measured. Kiriyama funnel (manufactured by Kiriyama Glass Works Co.) was used as the sample storage unit 111, and Kimwipes (manufactured by Nippon Paper Crecia Co., Ltd.) as the test solution supply member 113 was folded and placed in the Kiriyama funnel. As a test solution, 5 ml of pure water was dropped onto Kimwipes and the orally disintegrating tablet was placed.

Penetration of pure water from one end to the other end of the orally disintegrating tablet in contact with Kimwipes was confirmed and the water absorption time was measured. The swollen orally disintegrating tablet was removed from the Kimwipes with tweezers and its mass was measured.

Figure 5:
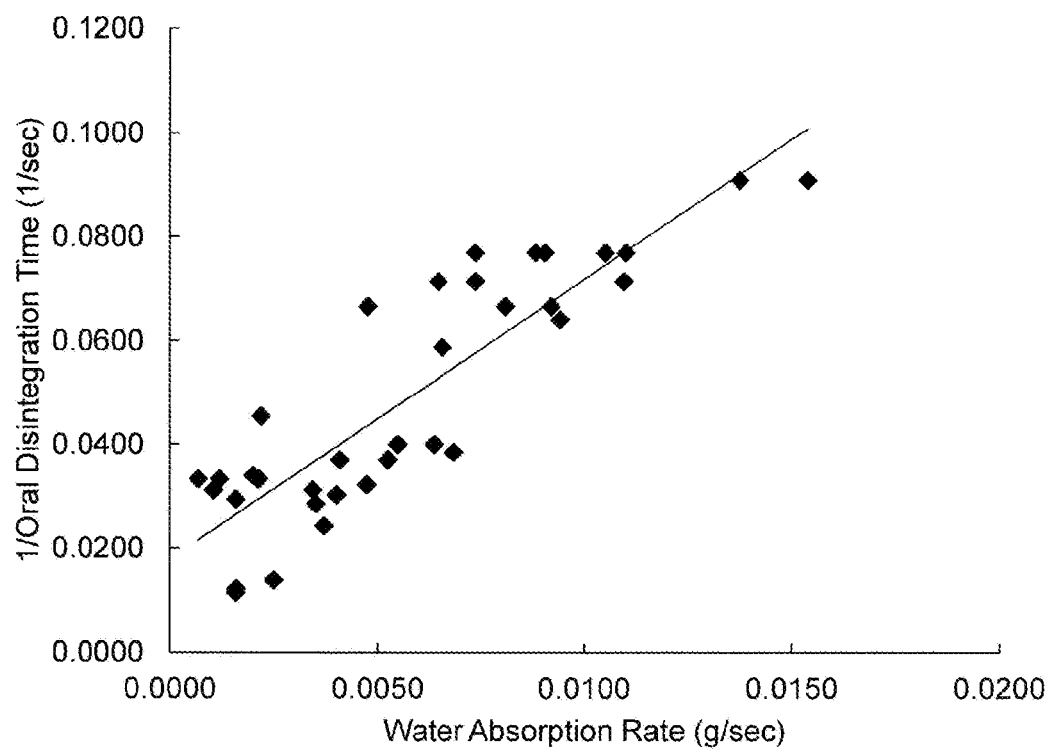
FIG. 5 is a correlation curve between the water absorption rate of an orally disintegrating tablet and the reciprocal of the oral disintegration time thereof according to one embodiment of the present invention.

The oral disintegration time was measured using an orally disintegrating tablet in the same lot as the orally disintegrating tablet whose water absorption time had been measured. The reciprocal of the oral disintegration time was plotted with respect to the water absorption rate of the orally disintegrating tablet. The correlation curve between the water absorption rate of the orally disintegrating tablet and the reciprocal of the oral disintegration time is shown in FIG. 5. In the correlation curve of this example in FIG. 5, the correlation coefficient was 0.8766, showing a good correlation.

Figure 6:
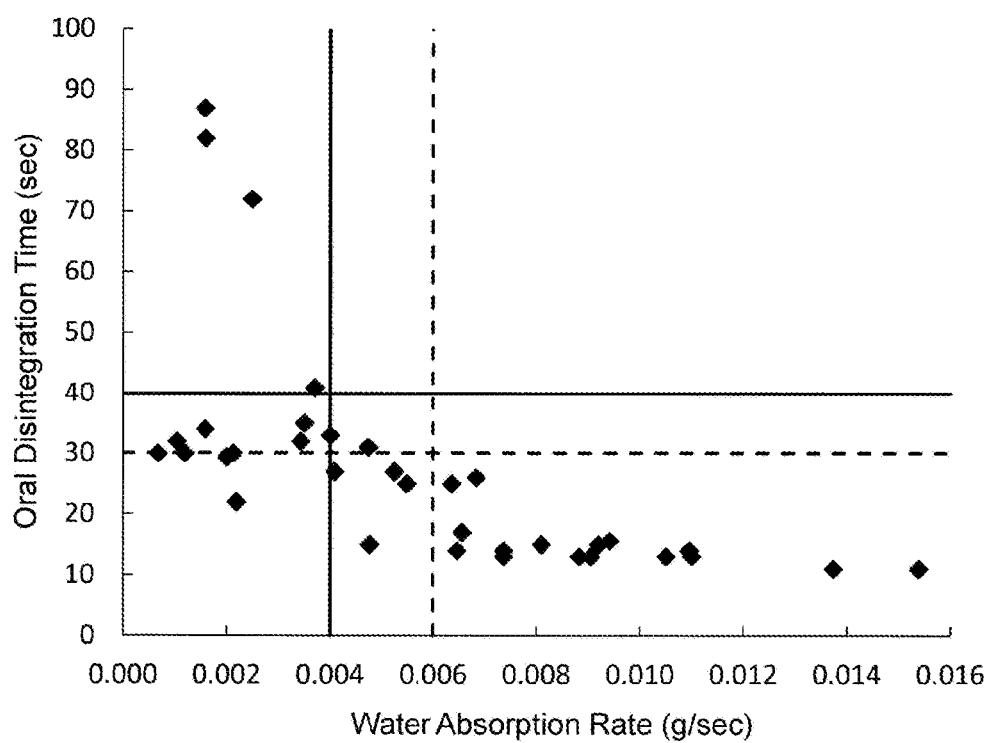
FIG. 6 is a correlation curve between the water absorption rate of an orally disintegrating tablet and the oral disintegration time thereof according to one embodiment of the present invention.

FIG. 6 shows a correlation curve between the water absorption rate of the orally disintegrating tablet and the oral disintegration time thereof according to the present example. In the correlation curve between the water absorption rate of the orally disintegrating tablet and the oral disintegration time thereof, the correlation is not high as compared with the correlation curve between the water absorption rate of the orally disintegrating tablet and the reciprocal of the oral disintegration time thereof in FIG. 5, that is, it turned out that a good correlation is obtained by plotting the reciprocal of the oral disintegration time. On the other hand, it was clarified from the correlation curve shown in FIG. 6 that the water absorption rate of the orally disintegrating tablet is adjusted to 0.004 g/sec or more in order to attain the oral disintegration time within 40 seconds. In contrast, it was clarified that the water absorption rate of the orally disintegrating tablet is adjusted to 0.006 g/sec or more in order to attain the oral disintegration time within 30 seconds.

Figure 7A:
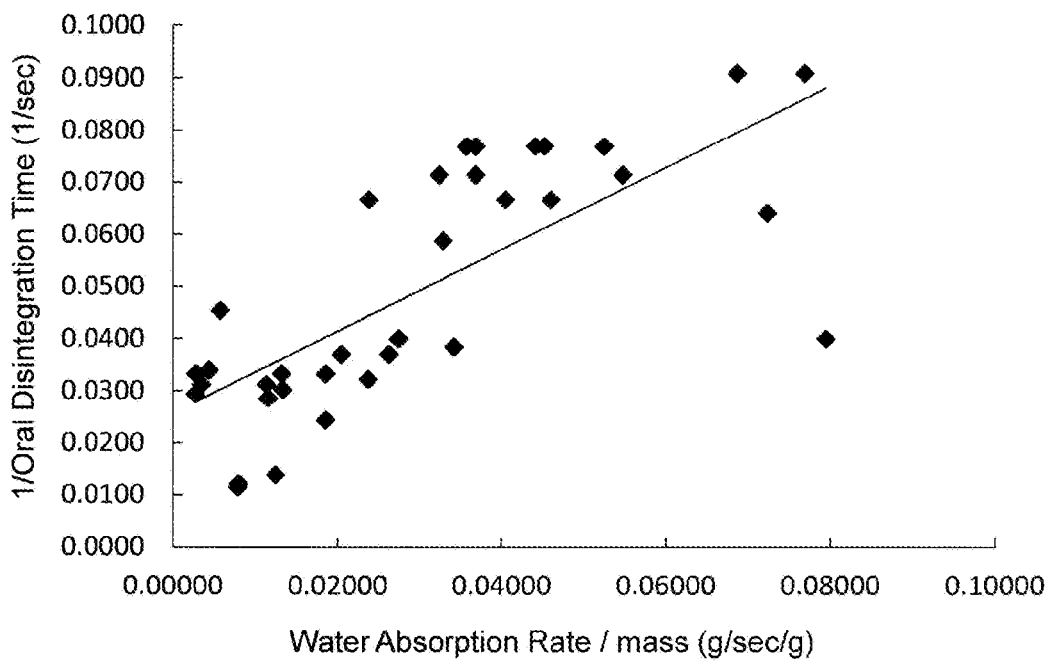
FIG. 7A shows a correlation curve obtained by normalizing the water absorption rate of an orally disintegrating tablet with the mass of the orally disintegrating tablet and plotting the reciprocal of the oral disintegration time.
Figure 7B:
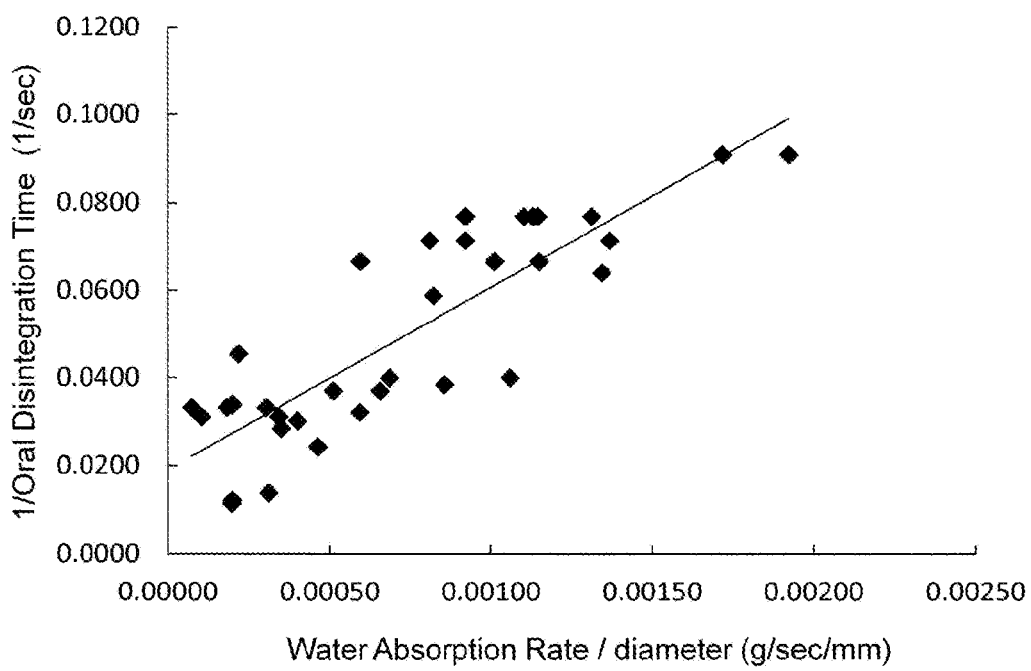
FIG. 7B shows a correlation curve obtained by normalizing the water absorption rate of an orally disintegrating tablet with the diameter of the orally disintegrating tablet and plotting the reciprocal of the oral disintegration time.
Figure 8A:
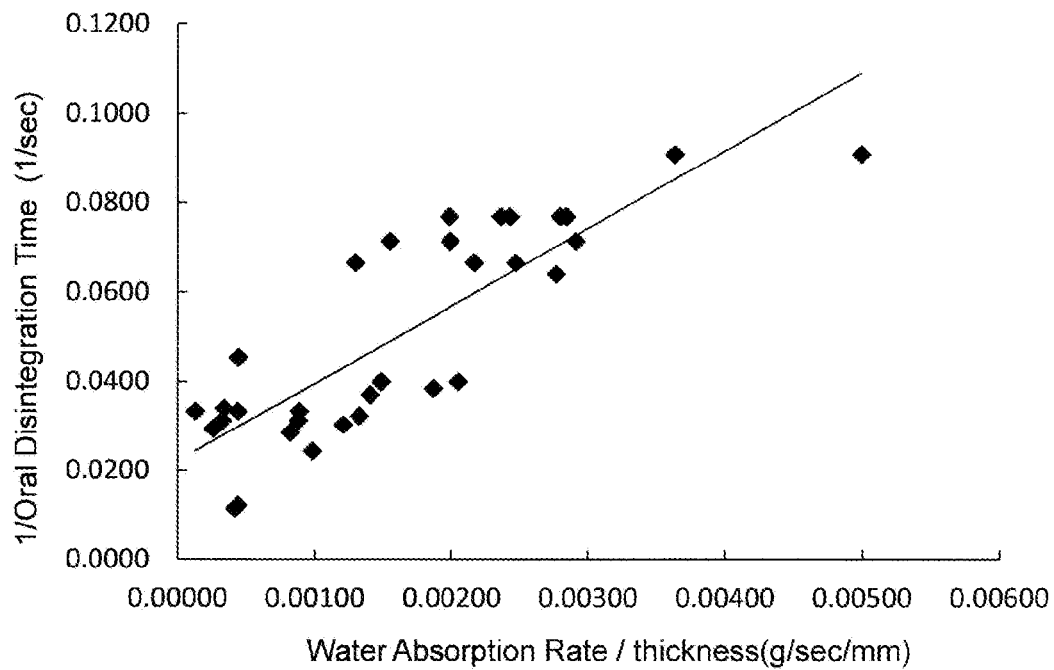
FIG. 8A shows a correlation curve obtained by normalizing the water absorption rate of an orally disintegrating tablet with the thickness of the orally disintegrating tablet and plotting the reciprocal of the oral disintegration time.
Figure 8B:
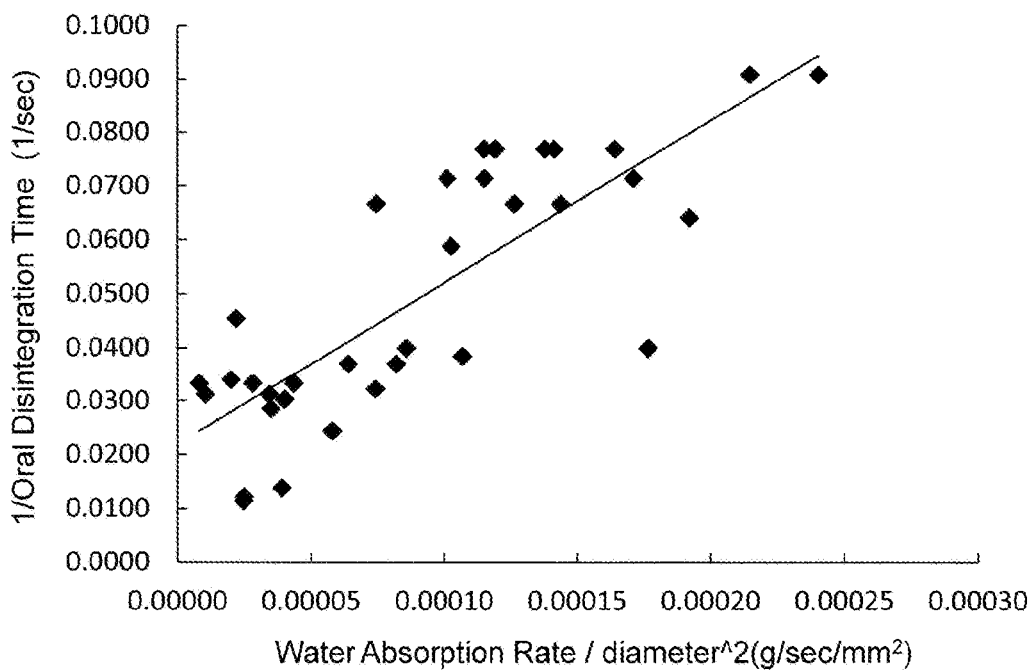
FIG. 8B shows a correlation curve obtained by normalizing the water absorption rate of an orally disintegrating tablet with the square of the diameter of the orally disintegrating tablet and plotting the reciprocal of the oral disintegration time.

For reference, a correlation curve with further normalized water absorption rate was examined using various parameters. FIGS. 7A, 7B, 8A and 8B show the correlation curves obtained. FIG. 7A is a correlation curve obtained by normalizing the water absorption rate of the orally disintegrating tablet with the mass of the orally disintegrating tablet and plotting the reciprocal of the oral disintegration time, and FIG. 7B is a correlation curve obtained by normalizing the water absorption rate of the orally disintegrating tablet with the diameter of the orally disintegrating tablet and plotting the reciprocal of the oral disintegration time. FIG. 8A is a correlation curve obtained by normalizing the water absorption rate of the orally disintegrating tablet with the thickness of the orally disintegrating tablet and plotting the reciprocal of the oral disintegration time, and FIG. 8B is a correlation curve obtained by normalizing the water absorption rate of the orally disintegrating tablet with the square of the diameter of the orally disintegrating tablet and plotting the reciprocal of the oral disintegration time.

In any of these correlation curves, the correlation was low as compared with the correlation curve between the water absorption rate of the orally disintegrating tablet and the reciprocal of the oral disintegration time thereof according to the present example, that is, it was clarified that these correlation curves are undesirable in the present invention.

According to one embodiment of the present invention, an evaluating method capable of properly evaluating the disintegration property in an orally disintegrating tablet of any formulation system is provided. Also, according to one embodiment of the present invention, an evaluating device is provided that can appropriately evaluate the disintegration property in an orally disintegrating tablet of any formulation system.

What is claimed is:

1. An orally disintegrating tablet evaluating method comprising:
   measuring a first mass of an orally disintegrating tablet;
   placing the orally disintegrating tablet on a preparation placement surface of a test solution supply unit, the test solution supply unit including a sample storage unit having a space to store the orally disintegrating tablet and a test solution supply member arranged on an inner bottom face of the sample storage unit, and the test solution supply member having the preparation placement surface and a test solution to supply the test solution to a first end of the orally disintegrating tablet;
   measuring a test solution absorption time to penetrate from the first end of the orally disintegrating tablet in contact with the preparation placement surface to a second end of the orally disintegrating tablet;
   measuring a second mass of the orally disintegrating tablet for which the time for the test solution to penetrate has been measured; and
   calculating a test solution absorption rate of the orally disintegrating tablet by the following formula (1);
   wherein
   the test solution is selected from the group consisting of water, artificial saliva and buffer solution,
   oral disintegration times of orally disintegrating tablets are separately measured,
   reciprocals of the oral disintegration times of orally disintegrating tablets are plotted with respect to test solution absorption rates of the orally disintegrating tablets calculated with the above defined calculation method using the formula (1), to obtain a correlation curve between the test solution absorption rates of the orally disintegrating tablets and the reciprocals of the oral disintegration times, and
   the orally disintegrating tablet is evaluated based on a test solution absorption rate of the orally disintegrating tablet of 0.004 g/sec:

the test solution absorption rate of the orally disintegrating tablet=(the second mass of the orally disintegrating tablet−the first mass of the orally disintegrating tablet)/(the time for the test solution to penetrate from the first end to the second end of the orally disintegrating tablet)      (1).

2. The orally disintegrating tablet evaluating method according to claim 1, wherein
   the test solution absorption rate of the orally disintegrating tablet for obtaining the oral disintegration time is calculated with the above defined calculation method using the formula (1), and
   the oral disintegration time corresponding to the the test solution absorption rate of the orally disintegrating tablet for obtaining the oral disintegration time is obtained from the correlation curve.

3. The orally disintegrating tablet evaluating method according to claim 1, wherein
   the orally disintegrating tablet has a shape having a major axis and a minor axis crossing the major axis,
   the orally disintegrating tablet is placed on the preparation placement surface of the test solution supply unit so that the major axis direction of the orally disintegrating tablet is substantially parallel to the preparation placement surface of the test solution supply unit, and
   the test solution absorption time for the test solution to penetrate from the first end of the orally disintegrating tablet in contact with the preparation placement surface to the second end of the orally disintegrating tablet furthest away from the first end in the minor axis direction of the orally disintegrating tablet is measured.

4. The orally disintegrating tablet evaluating method according to claim 3, wherein
   penetration of the test solution to the second end of the orally disintegrating tablet is judged by a change in a color tone of the second end of the orally disintegrating agent.

5. An orally disintegrating tablet evaluating device comprising:

a test solution supply unit, the test solution supply unit including a sample storage unit having a space to store an orally disintegrating tablet and a test solution supply member arranged on an inner bottom face of the sample storage unit, and the test solution supply member having the preparation placement surface and a test solution;

a test solution absorption time measuring unit, the test solution absorption time measuring unit including an image sensor to measure a color tone of the orally disintegrating table, and an analysis unit, the analysis unit including an arithmetic device to process an analysis program configured to analyze image data received from the test solution absorption time measuring unit, wherein the test solution is selected from the group consisting of water, artificial saliva and buffer solution, the test solution supply unit supplies the test solution to a first end of the orally disintegrating tablet in contact with a preparation placement surface, the test solution absorption time measuring unit measures a test solution absorption time for the test solution to penetrate from the first end of the orally disintegrating tablet to a second end of the orally disintegrating tablet, and the analysis unit calculates a test solution absorption rate of the orally disintegrating tablet by the following formula (1) using a first mass of the orally disintegrating tablet and a second mass of the orally disintegrating tablet for which the test solution absorption time for the test solution to penetrate has been measured, and evaluates the orally disintegrating tablet based on a test solution absorption rate of the orally disintegrating tablet of 0.004 g/sec:

the test solution absorption rate of the orally disintegrating tablet=(the second mass of the orally disintegrating tablet−the first mass of orally disintegrating tablet)/(the time for the test solution to penetrate from the first end to the second end of the orally disintegrating tablet)     (1).

6. The orally disintegrating tablet evaluating device according to claim 5, wherein the analysis unit receives an input of oral disintegration times of orally disintegrating tablets, and provides a correlation curve between the water absorption rates of the orally disintegrating tablets calculated with the above defined calculation method using the formula (1) and reciprocals of the oral disintegration times.

7. The orally disintegrating tablet evaluating device according to claim 6, wherein the analysis unit calculates the test solution absorption rate of the orally disintegrating tablet to obtain the oral disintegration time, and calculates the oral disintegration time corresponding to the test solution absorption rate of the orally disintegrating tablet to obtain the oral disintegration time from the correlation curve.

8. The orally disintegrating tablet evaluating device according to claim 5, wherein the analysis unit judges that the test solution has penetrated to the second end of the orally disintegrating tablet based on a change in the color tone of the second end of the orally disintegrating tablet.

* * * * *